US006869864B2

(12) United States Patent
Yim et al.

(10) Patent No.: US 6,869,864 B2
(45) Date of Patent: Mar. 22, 2005

(54) METHOD FOR PRODUCING QUANTUM DOT SILICATE THIN FILM FOR LIGHT EMITTING DEVICE

(75) Inventors: Jin Heong Yim, Daejeon-Shi (KR); Eun Joo Jang, Gyeonggi-Do (KR); Tae Kyung Ahn, Seoul (KR)

(73) Assignee: Samsung Electronics Co., Ltd., Kyungki-Do (KR)

( * ) Notice: Subject to any disclaimer, the term of this patent is extended or adjusted under 35 U.S.C. 154(b) by 0 days.

(21) Appl. No.: 10/734,230

(22) Filed: Dec. 15, 2003

(65) Prior Publication Data

US 2004/0266148 A1 Dec. 30, 2004

(30) Foreign Application Priority Data

Jun. 27, 2003 (KR) .................................. 10-2003-0042448

(51) Int. Cl.$^7$ .............................................. H01L 21/20
(52) U.S. Cl. ......................... 438/497; 438/478; 438/962
(58) Field of Search .................................. 438/497, 500, 438/478, 962, 46

(56) References Cited

U.S. PATENT DOCUMENTS

| 5,354,707 | A | * | 10/1994 | Chapple-Sokol et al. ..... 438/24 |
| 5,751,018 | A | | 5/1998 | Alivisatos et al. |
| 6,225,198 | B1 | * | 5/2001 | Alivisatos et al. .......... 438/497 |
| 6,251,303 | B1 | | 6/2001 | Bawendi et al. |
| 6,423,551 | B1 | * | 7/2002 | Weiss et al. ................. 436/518 |
| 6,444,143 | B2 | | 9/2002 | Bawendi et al. |
| 6,623,559 | B2 | * | 9/2003 | Huang ......................... 117/87 |
| 6,794,265 | B2 | * | 9/2004 | Lee et al. .................... 438/409 |

* cited by examiner

Primary Examiner—Matthew Smith
Assistant Examiner—Lex H. Malsawma
(74) Attorney, Agent, or Firm—Birch, Stewart, Kolasch & Birch, LLP

(57) ABSTRACT

A method for producing a quantum dot silicate thin film for light emitting devices. The quantum dot silicate thin film is produced by introducing a silane compound having a functional group capable of interacting with a quantum dot and at least one reactive group for a sol-gel process into the surface of the quantum dot or a matrix material for dispersing the quantum dot, thereby exhibiting excellent mechanical and thermal stability.

19 Claims, 5 Drawing Sheets

METHOD FOR PRODUCING QUANTUM DOT SILICATE THIN FILM FOR LIGHT EMITTING DEVICE

BACKGROUND OF THE INVENTION

This non-provisional application claims priority under 35 U.S.C. § 119(a) on Korean Patent Application No. 2003-42448 filed on Jun. 27, 2003, which is herein incorporated by reference.

FIELD OF THE INVENTION

The present invention relates to a method for producing a quantum dot silicate thin film for light emitting devices, and more particularly to a method for producing a quantum dot silicate thin film for light emitting devices with excellent mechanical and thermal stability by introducing a silane compound having a functional group capable of interacting with a quantum dot and at least one reactive group for a sol-gel process, into the surface of the quantum dot or a matrix material for dispersing the quantum dot.

DESCRIPTION OF THE RELATED ART

Quantum dots are nanometer-sized semiconducting materials which exhibit quantum confinement effects. When the quantum dots are irradiated by light from an excitation source to reach respective energy excited states, they emit energies corresponding to the respective energy band gaps. Accordingly, since the control over the size of the quantum dots effectively controls the corresponding band gaps, energies of various wavelength regions can be obtained.

Techniques for controlling the growth of quantum dots will be most important in the development of future semiconductor devices. MOCVD (metal organic chemical deposition), MBE (molecular beam epitaxy) and the like are recognized as techniques suitable for controlling the thickness of semiconductor thin films to the level of a monoatomic layer, and at the same time, for controlling the growth of quantum dots. However, quantum dots synthesized by a vapor phase process based on lattice mismatch have an advantage in terms of good crystallinity, but have a disadvantage in that the control of density and uniformity is difficult. Until now, it is known that devices fabricated by the above-mentioned techniques are unsuccessful in their commercialization.

In an effort to overcome the disadvantages and limitations of conventional techniques for growing quantum dots on a thin film by a vapor phase process, J. Am. Chem. Soc. 115, 8706–8715 (1993) discloses a method for synthesizing a quantum dot using a wet chemistry technique. Most wet chemistry techniques can control the size of quantum dots to the level of a few nanometers by depositing a precursor capable of growing quantum dot crystals in a coordinating organic solvent. As the quantum dot crystals are grown, the organic solvent is coordinated to the surface of the quantum dot crystals to act as a dispersant Coordinated quantum dots disclosed in U.S. Pat. Nos. 6,251,303 and 6,444,143 are readily dispersed in most organic solvents. When the organic materials coordinated to the surface of the quantum dots are displaced with charged materials, the surface displaced quantum dots are dispersible in aqueous solutions, as well as in organic solvents. Accordingly, the development of techniques capable of easily displacing such coordinated quantum dots allows the quantum dots to be utilized in a variety of applications, e.g., electronic circuits, polymeric materials, biomolecules, and the like.

In order to synthesize quantum dots of which the surface is capped with a dispersant and which is stably dispersed in a solution and to utilize them in various applications, it is important to modify the surface with a material compatible with subjects to be applied. For application of the quantum dots to EL devices, the quantum dots are mixed with various kinds of conductive polymers to exhibit luminescence properties of the quantum dots. At this time, the quantum dots are required to be homogeneously dispersed in a polymer matrix. For this purpose, the surface of the quantum dots is capped with a material compatible with the polymer or the polymer is displaced with molecules capable of readily capping on the surface of the quantum dots [J. Appl. Phys., Vol. 86, No. 8, 4390].

In addition, for application of quantum dots to biological systems, it is important to make the surface of the quantum dots hydrophilic. For this purpose, the quantum dots may be capped with a compound having sulfonate or acetate ions at the ends of the compound chain.

However, compound semiconductor quantum dots synthesized by currently used wet chemistry techniques (colloidal process) are limited to the fabrication of Group II and VI compound semiconductors. No research has been conducted on the fabrication of Group III, IV and V compound semiconductors.

The main advantage of the wet chemistry techniques is the excellent uniformity of quantum dots to be synthesized. This advantage is accomplished by centrifuging the synthesized quantum dots for selective precipitation, designing a precursor to be used, or controlling reaction conditions during synthesis of the quantum dots. However, the reconfiguration of the quantum dots synthesized by the wet chemistry techniques is required to apply the quantum dots to most devices. Satisfactory techniques for reconfiguring quantum dots having a size of a few nanometers into a constant aligned structure are not yet known. U.S. Pat. No. 5,751,018 discloses a method for forming a single film of quantum dots by bonding a sulfur atom at one end of a dithiol compound to the surface of a metal such as gold or aluminum used as a substrate to form a monolayer on the substrate, and bonding another sulfur atom at the other end of the dithiol compound to the surface of compound semiconductor quantum dots. The sulfur atoms of the dithiol compound can covalently bind to the metal. Multilayers of quantum dots capable of improving the luminescence efficiency have not yet been developed. Furthermore, Journal of Applied Polymer, Vol 86., No 8 (1999) describes quantum dots dispersed in an organic polymer to apply the quantum dots to organic EL devices. However, this simple mixing of the quantum dots and the organic polymer cannot increase the concentration of the quantum dots and improve the thermal stability of the quantum dots. Accordingly, thin films produced from the quantum dots are limited in their applicability to various devices.

SUMMARY OF THE INVENTION

A feature of the present invention is to provide a quantum dot thin film having a high luminescence efficiency in which quantum dots are spaced apart from each other at a particular bonding distance and linked through siloxane covalent bonds formed therebetween to form a single film of the quantum dots, thereby increasing the density of the quantum dots in the thin film.

Another feature of the present invention is to provide a method for producing a quantum dot thin film which can maintain a bandgap of a single quantum dot without any clustering of quantum dots by mixing quantum dots and a silicate precursor having a functional group capable of interacting with the quantum dots.

In accordance with the features of the present invention, there is provided a method for producing a quantum dot silicate thin film which comprises the steps of: displacing the surface of semiconductor quantum dots having a size of 1–100 mm synthesized by a wet chemistry technique with a silane compound having a phosphine-, amine- or thiol-based functional group and at least one reactive group for a sol-gel process; subjecting the surface-displaced quantum dots to a sol-gel process, followed by coating onto a substrate, or coating the surface-displaced quantum dots onto a substrate, followed by subjecting it to a sol-gel process; and heat-treating the coated substrate.

In accordance with the other feature of the present invention, there is further provided a method for producing a quantum dot silicate thin film which comprises the steps of: subjecting a silane compound and a siloxane-based monomer to a sol-gel process to prepare a silicate precursor, the silane compound having a phosphine-, amine- or thiol-based functional group and at least one reactive group for a sol-gel process; mixing the silicate precursor and semiconductor quantum dots having a size of 1–1000 nm synthesized by a wet chemistry technique; coating the mixture onto a substrate; and heat-treating the coated substrate.

Further scope of applicability of the present invention will become apparent from the detailed description given hereinafter. However, it should be understood that the detailed description and specific examples, while indicating preferred embodiments of the invention, are given by way of illustration only, since various changes and modifications within the spirit and scope of the invention will become apparent to those skilled in the art from this detailed description.

BRIEF DESCRIPTION OF THE DRAWINGS

The present invention will become more fully understood from the detailed description given hereinbelow and the accompanying drawings which are given by way of illustration only, and thus are not limitative of the present invention, and wherein.

DESCRIPTION OF THE PREFERRED EMBODIMENTS

Figure 1:
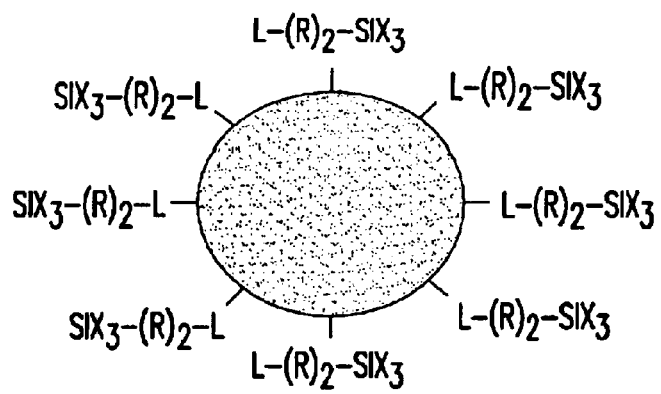
FIG. 1 is a diagram schematically showing the structure of a quantum dot displaced with a silane compound having at least one reactive group for a sol-gel process.

Hereinafter, the present invention will be explained in more detail.

The first embodiment of the present invention relates to a method for producing a quantum dot thin film with excellent mechanical and thermal stability by displacing the surface of nanometer-sized compound semiconductor quantum dots synthesized by a wet chemistry technique with a silane compound having at least one reactive group for a sol-gel process, and subjecting the surface-displaced quantum dots to a sol-gel process.

The method of the present invention will be explained in terms of the respective steps.

Synthesis of Quantum Dots

In the present invention, the synthesis of quantum dots can be performed by all techniques known in the art, and thus is not limited to the procedure as described below.

For the synthesis of nanometer-sized quantum dots in the state of a colloid by a wet chemistry technique, a solvent capable of stably dispersing quantum dots is used. The solvent used in the present invention must be able to be coordinated to the surface of quantum dots, and have a bulkiness to the extent that it can control the growth rate of quantum dot crystals. In addition, the solvent must be stable at the temperature for growing the crystals, and be able to disperse colloidal particles at a state coordinated with quantum dots. Alkyl phosphines, alkyl phosphine oxides, alkyl amines, etc., can be used as the solvent. Preferably, phosphine, phosphine oxide, or a bulky alkyl amine having an alkyl group of about 8–16 carbon atoms and having a high boiling point is used alone or in combination as the solvent.

The solvent is relatively stable in air, but may be oxidized at high temperature. Accordingly, the reaction is processed under an inert atmosphere, e.g., nitrogen or argon. If necessary, pressurization can be added.

The reaction is carried out in the solvent under appropriate reaction conditions, of atmospheric pressure and temperature. Preferably, the reaction temperature distribution is narrow. The reaction temperature is dependent on the growth rate of the crystals, and varies according to materials to be synthesized. The reaction temperature is commonly in the range of 25–500° C., and preferably 25–350° C. When the reaction temperature is maintained to be constant, a quantum dot precursor is added. At this time, it is important to control the addition rate so that the precursor is introduced at one time. The quantum dot precursor is prepared in accordance with already known processes in the: art. For example, the quantum dot precursor may be prepared by adding a metal precursor and a chalcogenide precursor separately and reacting the mixture [J. Am. Chem. Soc. 115, 8706–8715(1993)]. In addition, the quantum dot precursor may be prepared by pyrolyzing a single precursor [J. Mater. Chem., 9, 2433–2437 (1999)]. In this case, a material which can readily disperse the precursor is used as a solvent. The solvent also should have a low viscosity, sufficient to control the feeding rate of the precursor solution and be stable during the reaction. Specific examples of the solvent include pyridine, alkyl amines, alkyl phosphines and the like. A stirrer for rapidly dispersing the precursor in a reactor after feeding of the precursor, and a vent for exhausting gasses generated during the reaction must be equipped in the reactor. After the mixture is maintained for a predetermined time so that quantum dot are grown in the form of a crystal, the reaction is fished. Alternatively, in the case of synthesizing quantum dots in the form of a core-shell, an inorganic precursor is further added to coat the core surface. When a precursor for constituting a shell is added, the precursor must be slowly introduced below a certain concentration so that it is deposited onto the core surface without formation of additional cores.

The reaction temperature is then suddenly cooled to quench the growth of the quantum dot crystals. For this purpose, an organic solvent having a relatively low boiling point is further added. Since the organic solvent absorbs heat through vaporization, the growth of the crystals can be quenched. Accordingly, the control of the amount of the solvent added enables the reaction temperature to be lowered to a temperature at which the growth of the crystals is quenched.

Since the quantum dots thus synthesized are dispersed in a colloidal state in the solvent, they can be separated from the solvent by centrifugation. At this step, a narrow size distribution of the quantum dots can be accomplished by selective precipitation and thus the uniformity of the quantum dots is improved. Selective precipitation refers to a process in which a mixture of a solvent having a high affinity and another solvent having a low affinity for materials capped onto the surface of the quantum dots in an appropriate ratio controls the precipitation rate of quantum dots upon centrifugation, thereby separating quantum dots having a constant size distribution. Because the surface of the quantum dots separated by centrifugation is capped with organic materials, the quantum dots are readily dispersible in most organic solvents.

The quantum dots may have various shapes, e.g., spheres, rods, stars, etc., depending on the reaction conditions, and the shapes and the crystal surface of the quantum dots can be determined by the resolution transmission electron microscopy (HRTEM).

Recently, some recent literature reports have been made of nanometer-sized particles, synthesized by a wet chemistry technique, capable of emitting visible light, e.g., composed of cadmium sulfide (CdS), cadmium selenide (CdSe), cadmium telluride, (CdTe), zinc sulfide (ZnS), zinc selenide (ZnSe) and zinc telluride (ZnTe), and particles capable of emitting light in the infrared range, e.g., composed of mercury telluride (HgTe).

Displacement of Quantum Dot Surface

The surface of the quantum dots thus synthesized is modified by a silane compound having a phosphine-, amine- or amine-based functional group and at least one reactive group for a sol-gel process.

The silane compound is preferably represented by the following formula 1:

L-(B)$_n$—SiR$_m$X$_{3-m}$    [Formula 1]

wherein L is a thiol group, a dialkylphosphinyl group having 1–5 carbon atoms, or a dialkylamine group having 1–5 carbon atoms; B is methylene or siloxy (—Si—O—) group; n is an integer of 1 to 50; X is a halogen atom or an alkoxy group having 1–10 carbon atoms; R is an alkyl group having 1–10 carbon atoms; and m is an integer of 0 to 2.

L defined in the formula 1 acts as a functional group capable of bonding to the surface of the quantum dots, X refers to a reactive group for a sol-gel process, and B functions as a bridging moiety for maintaining a constant distance through siloxane bonds formed between quantum dots by a subsequent sol-gel process. The structure of the quantum dot displaced with the silane compound is schematically shown in FIG. 1.

Specific examples of the silane compound include, but are not limited to, mercaptomethylmethyldimethoxysilane, 3-mercaptopropylmethyldimethoxysilane, 3-mercaptopropyltriethoxysilane, 3-mercaptopropyltrimethoxysilane, 2-diphenylphosphinoethyltriethoxysilane, diphenylphosphinoethyldimethylethoxysilane, 3-aminopropylmethyldiethoxysilane, 3-aminopropyldimethylethoxysilane, 3-aminopropyltriethoxysilane, 3-aminopropyltrimethoxysilane, 3-aminobutyltrimethoxysilane, 3-(m-aminophenoxy)propyltrimethoxysilane, n-(2-aminoethyl)-3-aminopropylmethyldimethoxysilane, etc.

The displacement of the quantum dot surface with the silane compound is carried out by dispersing the quantum dots in a solution containing the silane compound at high concentration, followed by refluxing at 25–200° C., preferably 25–100° C. and centrifuging. By repetition of the procedure, materials capped to the surface of the quantum dots are removed and the quantum dots are displaced with the silane compound. When the capped materials are so strongly coordinated to the surface of the quantum dots that the displacement with the silane compound is difficult, the surface is first modified using pyridine having a low boiling point. Subsequently, the pyridine is evaporated under vacuum. Then, the surface-modified quantum dots are dispersed in a solution containing the silane compound, followed by several treatments of refluxing and centrifugation.

Production of Quantum Dot Thin Film

Since reactive groups for a sol-gel process are disposed at the ends of the quantum dots, siloxane bonds between the quantum dots can be formed by a sol-gel process under acidic or basic conditions.

For producing a quantum dot thin film, quantum dots are dispersed in a solvent where a sol-gel process can take place. An acid or base catalyst is added to the dispersion to carry out the sol-gel process. When the reaction mixture has an increased viscosity, it is coated onto a substrate. Finally, the coated substrate is heat-treated to produce a quantum dot thin film. Alternatively, after quantum dots to which reactive groups for a sol-gel process are coordinated are coated onto a substrate, they are subjected to a sol-gel process on the substrate by treating with an acid or base, and heat-treatment for producing a quantum dot thin film.

Figure 2A:
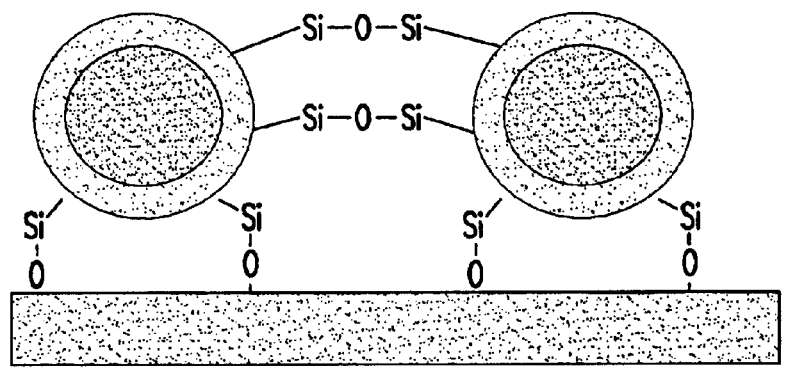
FIG. 2 is a diagram schematically showing the structure of a quantum dot thin film in which siloxane bonds are formed between surface-modified quantum dots.
Figure 2:
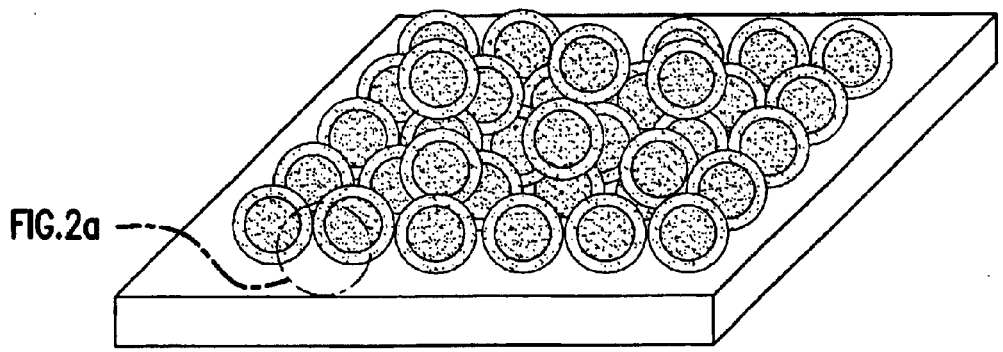

The structure of the quantum dot thin film thus produced is schematically shown in FIG. 2.

The second embodiment of the present invention relates to the method for producing a quantum dot silicate thin film by dispersing quantum dots synthesized by a wet chemistry technique in a silicate precursor compatible with the quantum dots, and coating the dispersion onto a substrate. The synthesis of the quantum dots is as explained above. The subsequent steps will be described below.

Preparation of Silicat Precursor

As a silicate precursor, a siloxane resin having a weight average molecular weight of about 1,000–100,000 and preferably about 1,000–10,000, is used. The silicate precursor is prepared by subjecting a silane compound having a phosphine-, amine- or thiol-based functional group and at least one reactive group for a sol-gel process, and a siloxane-based monomer to a sol-gel process under acidic or basic conditions. At this time, the sol-gel process involves hydrolysis and condensation. The molar ratio of the silane compound and the siloxane-based monomer is, preferably, 99:1–1:99.

As the siloxane-based monomer, a ring-structured or cage-structured siloxane monomer is used alone or in combination. If necessary, a silane compound can be added to the sol-gel process as a monomer.

The ring-structured siloxane monomer is a compound in which adjacent silicon atoms are bridged by one oxygen atom, represented by the following formula 2:

[Formula 2]

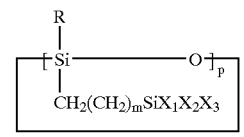

wherein R is a hydrogen atom, an alkyl group having 1–3 carbon atoms, a cycloalkyl group having 3–10 carbon atoms or an aryl group having 6–15 carbon atoms; X$_1$, X$_2$ and X$_3$ are each independently an alkyl group having 1–3 carbon atoms, an alkoxy group having 1–10 carbon atoms or a halogen atom, provided that at least one of $X_1$, $X_2$ and $X_3$ is hydrolysable; p is an integer of 3 to 8; and m is an integer of 0 to 10.

The ring-structured siloxane monomer may be produced by hydrosilylation in the presence of a metal catalyst, but is not especially limited thereto.

The cage-structured siloxane monomer includes compounds in which adjacent silicon atoms are bridged by one oxygen atom, represented by the following formulae 3 to 5:

[Formula 3]

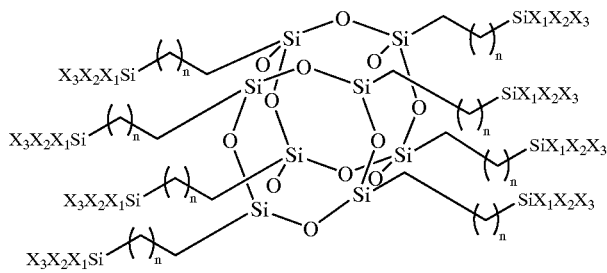

[Formula 4]

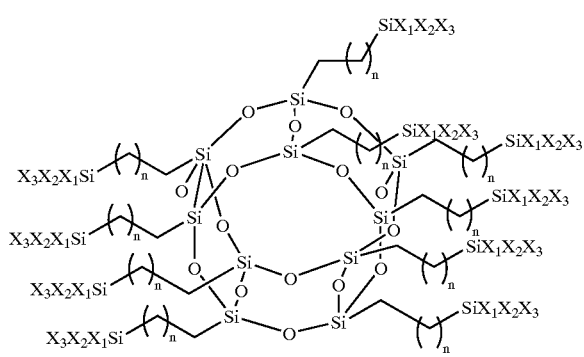

[Formula 5]

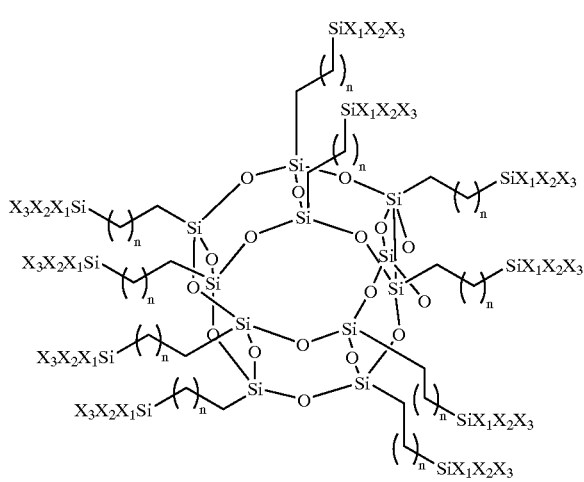

wherein $X_1$, $X_2$ and $X_3$ are each independently an alkyl group having 1–3 carbon atoms, an alkoxy group having 1–10 carbon atoms or an halogen atom, provided that at least one of $X_1$, $X_2$ and $X_3$ is hydrolysable; and n is an integer of 0 to 10.

The cage-structured siloxane monomer may be produced by hydrosilylation in the presence of a metal catalyst, but is not especially limited thereto.

The silane compound includes those represented by the following formulae 6 to 8:

$SiX_1X_2X_3X_4$      [Formula 6]

$R_1SiX_1X_2X_3$      [Formula 7]

$R_1R_2SiX_1X_2$      [Formula 8]

wherein $R_1$ and $R_2$ are each independently a hydrogen atom, an alkyl group having 1–3 carbon atoms, a cycloalkyl group having 3–10 carbon atoms or an aryl group having 6–15 carbon atoms; and $X_1$, $X_2$, $X_3$ and $X_4$ are each independently an alkoxy group having 1–10 carbon atoms or a halogen atom.

Examples of the acid catalyst used in the condensation for preparing the matrix monomer preferably include, but are not limited to, hydrochloric acid, benzenesulfonic acid, oxalic acid, formic acid and mixtures thereof. Examples of the base catalyst include, but are not limited to, potassium hydroxide, sodium hydroxide, triethylamine, sodium bicarbonate, pyridine and mixtures thereof. The molar ratio of the catalyst to the monomer is within the range of 1:0.000001–1:10.-

The equivalent amount of water used during the hydrolysis and condensation is in the range of 1.0–100.0 and preferably 1.0–10.0, relative to the reactive groups present in the monomer. The reaction temperature is in the range of 0–200° C., and preferably 50–110° C., and the reaction time is preferably in the range of 1–100 hours, and more preferably 5–24 hours.

Production of Quantum Dot Thin Film

The silicate precursor and the quantum dots are mixed, coated onto a substrate, and heat-treated to produce a quantum dot silicate thin film of the present invention. The silicate precursor and the quantum dots are mixed in the weight ratio of 99:1–50:50.

Examples of the substrate on which the quantum dot thin film is produced include glass, quartz, silicon (Si) wafers, silica-coated substrates, alumina-coated substrates, etc.

The coating of the mixture can be carried out by commonly used coating processes, e.g., drop casting, spin coating, dip coating, spray coating, flow coating, screen printing, etc., but is not limited to these processes. Drop casting and spin coating are preferred. In the case of coating the mixture using a solvent, the solvent is evaporated after coating to deposit a mixed composition film on the substrate. For evaporating the solvent from the substrate, the substrate containing the solvent is exposed to the ambient surroundings (simple air drying), dried under vacuum at the early step of a curing process discussed below, or gently heated to 100° C. or less.

Thereafter, the film thus produced is cured by heating to 150° C.–600° C. and preferably 200–450° C. for a particular time to form an insoluble film having no cracks. The heating may be carried out under an inert atmosphere or under vacuum. The curing is carried out for 100 hours or less, and preferably 30 minutes–24 hours. As used herein, the phrase film having no cracks' means a film in which no cracks are observed under an optical microscope (×1,000). The insoluble film refers to a film which is not substantially dissolved in the solvent used to deposit the film or solvents commonly used to apply a resin.

The present invention will now be described in more detail with reference to the following Examples. However, these Examples are given for the purpose of illustration and are not to be construed as limiting the scope of the invention.

EXAMPLE 1

Synthesis of Yellow Light-Emitting Cadmium Sulfide Quantum Dots 2.5 ml of trioctyl amine as a solvent is placed in a 25 ml flask equipped with a reflux condenser, and the temperature of the flask is adjusted to 180° C. with stirring. A solution of 50 mg of cadmium dithio diethyl carbamate in 0.9 ml of trioctyl phosphine is rapidly injected into the flask. After 10 minutes, a solution of 20 mg of zinc dithio diethyl carbamate in 0.3 ml of trioctyl phosphine is slowly added dropwise. About 5 minutes after the addition of zinc dithio diethyl carbamate is completed, the temperature of the reactor is cooled and then ethanol is added to quench the reaction. Quantum dots are obtained from the resulting mixture through centrifugation and dispersed in toluene. The photoluminescence spectrum confirmed that the compound semiconductor quantum dots emits yellow light at 536 nm.

EXAMPLE 2

Synthesis of Blue Light-Emitting Cadmium Sulfide Quantum Dots

The procedure is carried out in the same manner as in Example 1, except that after a solution of cadmium carbamate in trioctyl phosphine is rapidly injected, the reaction is maintained for about 7 minutes. Quantum dots are obtained from the resulting mixture through centrifugation and dispersed in toluene. The photoluminescence spectrum confirmed that the compound semiconductor emits blue light at 470 nm.

EXAMPLE 3

Figure 3:
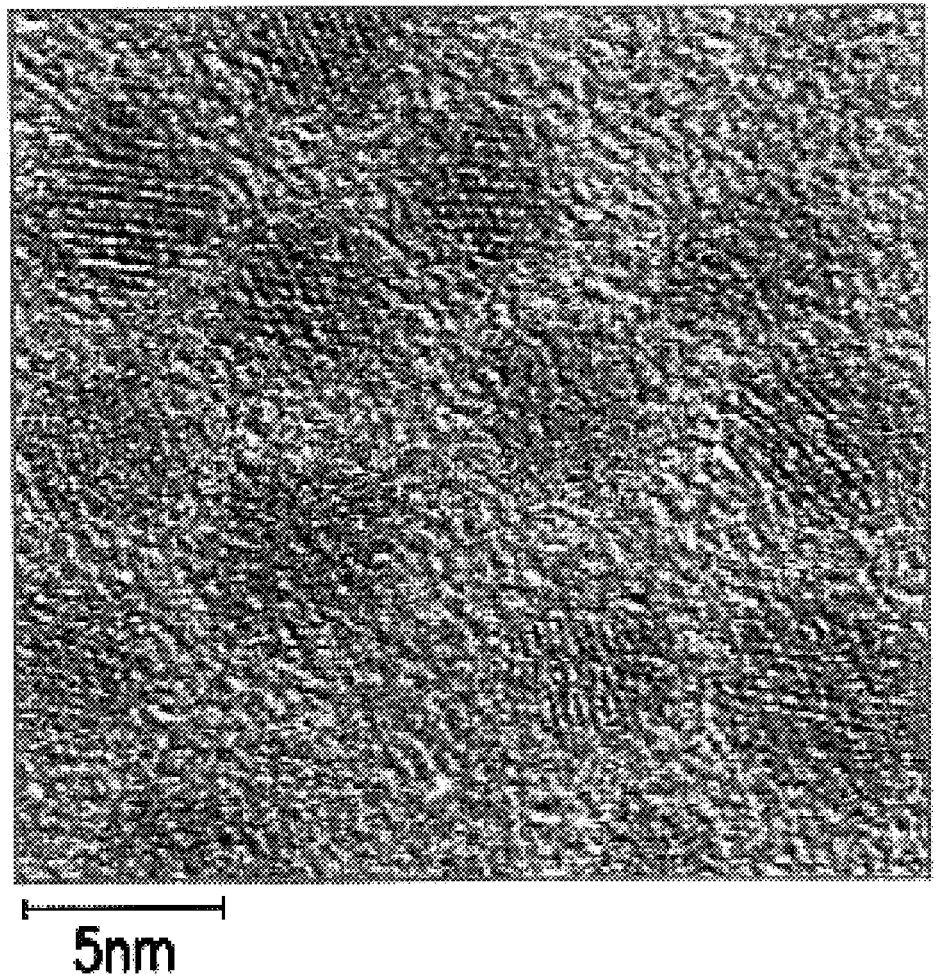
FIG. 3 is a transmission electron microscopy (TEM) image of quantum dots synthesized in Example 3 of the present invention.

Displacement of Quantum Dot Surface with Alkoxy Silane Compound 3-mercaptopropyltrimethoxysilane is added to a solution of the cadmium sulfide quantum dots synthesized in Example 1 until the concentration reached 5 mM. The resulting mixture is refluxed at 70° C. for 24 hours with stirring. The mixture is centrifuged to remove a dispersant separated from the surface of the quantum dots. The separated quantum dots are dispersed in toluene, and then 3-mercaptopropyltrimethoxysilane is added thereto until the concentration reached 5 mM. The mixture is refluxed for 24 hours with stirring. This procedure is repeated several times to prepare quantum dots of which the surface is displaced with mercaptopropylmethoxysilane. After centrifuging, the surface-displaced quantum dots are dispersed in butanol for stable storage. High resolution transmission electron microscopy (HRTEM) reveals that quantum dots having a diameter of 3 nm are present, as depicted in FIG. 3.

Figure 4A:
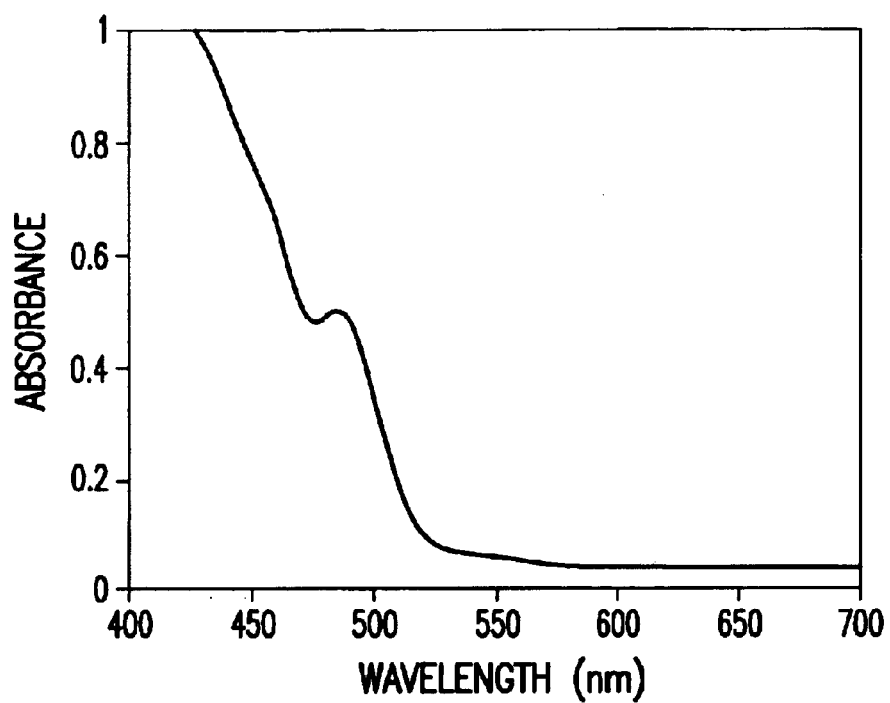
FIGS. 4a and 4b are a UV absorption spectrum and a photoluminescence spectrum of quantum dots synthesized in Example 3 of the present invention, respectively.
Figure 4B:
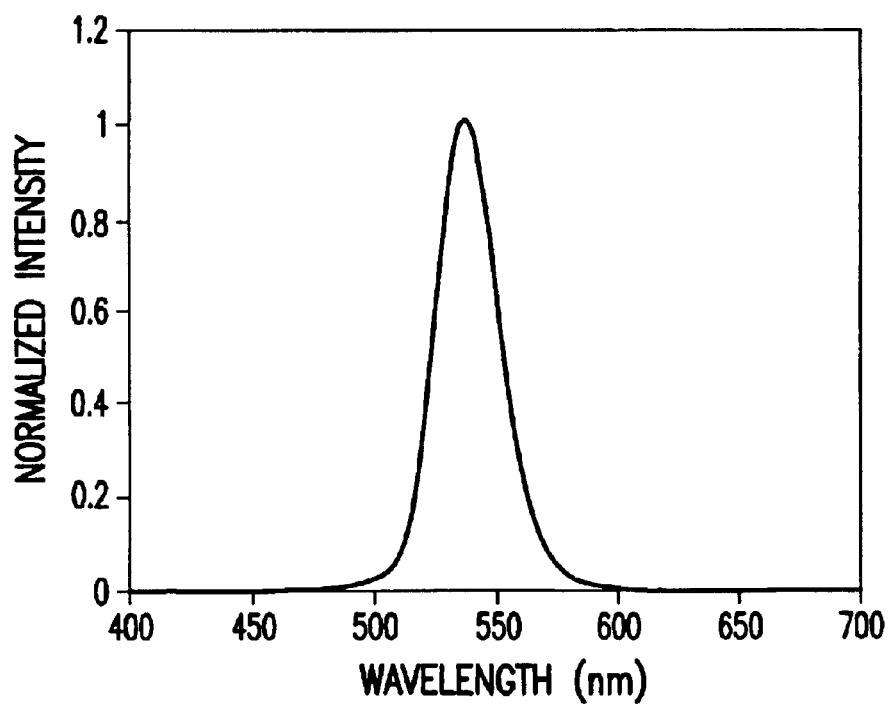

FIGS. 4a and 4b show a UV absorption spectrum and a photoluminescence spectrum of the quantum dot solution, respectively. The UV absorption is observed at around 398 nm (FIG. 4a), and the photoluminescence is observed at around 536 nm (FIG. 4b). These wavelength regions are coincident with those observed in the quantum dots undisplaced with 3-mercaptopropyltrimethoxysilane.

Figure 5A:
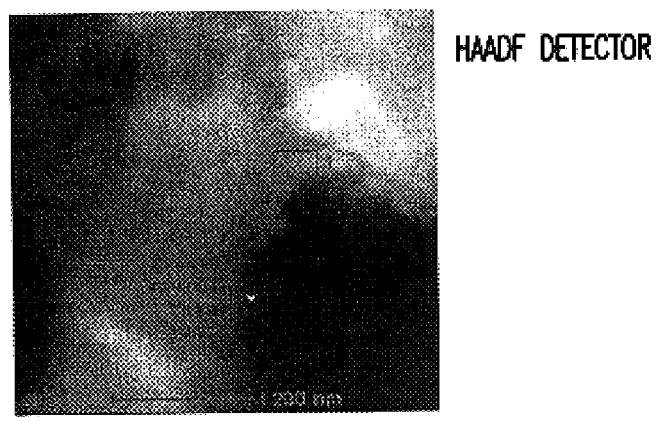
FIG. 5 is a diagram showing the TEM-EDS analytical results of quantum dots synthesized in Example 3 of the present invention.
Figure 5B:
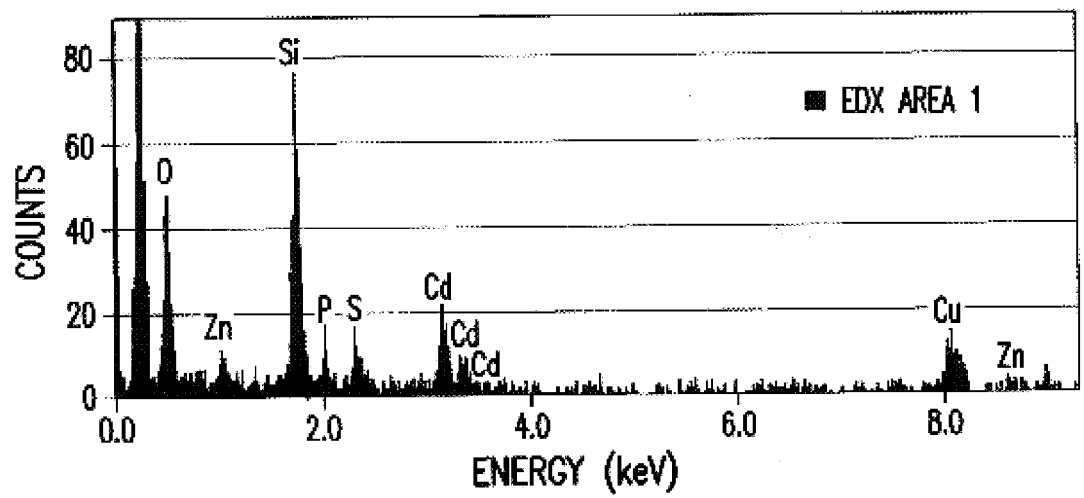

FIG. 5 is a diagram showing the TEM-EDS Transmission Electron Microscope-Energy Dispersive X-ray Spectrometer) analytical results of the quantum dots. As can be seen from FIG. 5, silicon atoms are present on the quantum dot surface, which indicates the presence of 3-mercaptopropyltrimethoxysilane on the surface of the quantum dots.

EXAMPLE 4

Production of Yellow Light-Emitting Quantum Dot Silicate Thin Film

The quantum dots synthesized in Example 3 are subjected to a drop casting process to coat the quantum dots onto a substrate. First, the quantum dots are subjected to a sol-gel process at 70° C. and pH 8 for 1 hour to induce condensation between the quantum dots dispersed in butanol, and then drop-cast on a glass substrate. Next, the substrate is dried in air for 24 hours and heat-treated at 250° C. for 1 hour to complete the sol-gel process, thereby producing a quantum dot silicate thin film.

The photoluminescence spectrum of the thin film shows that a sharp PL peak is observed at 559 nm. This confirms that the light-emitting wavelength of the quantum dots present in the solution is well maintained.

EXAMPLE 5

Production of Blue Light-Emitting Quantum Dot Silicate Thin Film

Figure 6:
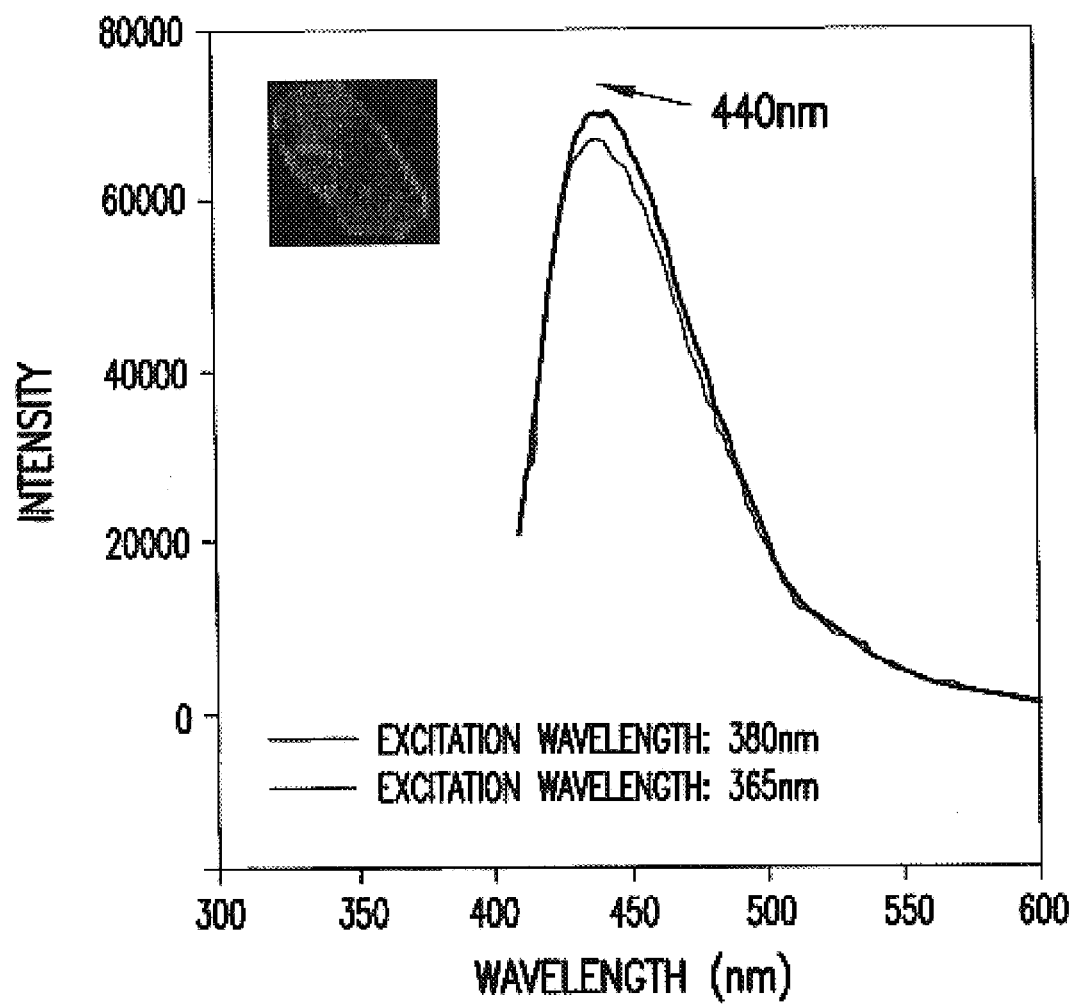
FIG. 6 is a photoluminescence spectrum of a quantum dot thin film produced in Example 5 of the present invention.

To prepare a silicate precursor capable of dispersing the quantum dots, 1 g of 2,4,6,8-tetramethyl-2,4,6,8-tetra (trimethoxysilylethyl) cyclotetrasiloxane as a monomer and 4 g of 3-mercaptopropyltrimethoxy silane are dissolved in 7.5 ml of butanol in a 50 ml reactor at room temperature. The temperature of the reactor is cooled to 0° C., and then 2.64 g of water and 0.25 g of 0.01M hydrochloric acid are slowly added to the reactor. Then, the temperature of the reactor is raised to 90° C., and the mixture is reacted for 1.5 hours to yield a siloxane copolymer. The siloxane copolymer is dried under vacuum at room temperature for 30 minutes to prepare a viscous silicate precursor. The silicate precursor thus prepared and the blue quantum dots synthesized in Example 2 are added to a solvent so that the content of the quantum dots reaches 15 wt % based on the total solid content. The quantum dot solution is subjected to a drop casting process to coat the quantum dots onto a substrate. The coated substrate is dried in air for 72 hours and heat-treated at 250° C. for 1 hour to complete the sol-gel process, thereby producing a quantum dot silicate thin film. FIG. 6 is a photoluminescence spectrum of the quantum dot thin film. The photoluminescence spectrum of the thin film showed that a sharp peak is observed at 440 nm, indicating that the light-emitting wavelength of the quantum dots present in the solution is well maintained.

Although the preferred embodiments of the present invention have been disclosed for illustrative purposes, those skilled in the art will appreciate that various modifications, additions and substitutions are possible, without departing from the spirit and scope of the invention as defined in the accompanying claims.

What is claimed is:

1. A method for producing a quantum dot silicate thin film which comprises the steps of:
    displacing the surface of semiconductor quantum dots having a size of 1~100 nm and synthesized by a wet chemistry technique with a silane compound having a phosphine-, amine- or thiol-based functional group and at least one reactive group for a subsequent sol-gel process;
    subjecting the surface-displaced quantum dots to the sol-gel process, followed by coating onto a substrate, or coating the surface-displaced quantum dots onto a substrate, followed by subjecting them to the sol-gel process; and
    heat-treating the coated substrate.

2. The method for producing a quantum dot silicate thin film according to claim 1, wherein the quantum dots are made of a material selected from the group consisting of cadmium selenide (CdSe), cadmium sulfide (CdS), cadmium telluride, (CdTe), zinc selenide (ZnSe), zinc sulfide (ZnS), zinc telluride (ZnTe), mercury telluride (HgTe) and mixtures thereof.

3. The method for producing a quantum dot silicate thin film according to claim 1, wherein the silane compound having a phosphine-, amine- or thiol-based functional group and at least one reactive group for a sol-gel process is represented by the following formula 1:

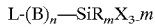  [Formula 1]

wherein L is a thiol group, a dialkylphosphinyl group having 1~5 carbon atoms, or a dialkylamine group having 1~5 carbon atoms; B is methylene or siloxy (—Si—O—) group; n is an integer of 1 to 50; X is a halogen atom or an alkoxy group having 1~10 carbon atoms; R is an alkyl group having 1~10 carbon atoms; and m is an integer of 0 to 2.

4. The method for producing a quantum dot silicate thin film according to claim 3, wherein the silane compound is at least one compound selected from the group consisting of mercaptomethylmethyldimethoxysilane, 3-mercaptopropylmethyldimethoxysilane, 3-mercaptopropyltriethoxysilane, 3-mercaptopropyltriethoxysilane, 2-diphenylphosphinoethyltriethoxysilane, diphenylphosphinoethyldimethylethoxysilane, 3-aminopropylmethyldiethoxysilane, 3-aminopropyldimethylethoxysilane, 3-aminopropyltriethoxysilane, 3-aminopropyltrimethoxysilane, 3-aminobutyltrimethoxysilane, 3-(m-aminophenoxy) propyltrimethoxysilane and n(2-aminoethyl)-3-aminopropylmethyldimethoxysilane.

5. The method for producing a quantum dot silicate thin film according to claim 1, wherein the substrate on which the quantum dot thin film is produced is glass, quartz, a silicon (Si) wafer, a silica-coated substrate or an alumina-coated substrate.

6. The method for producing a quantum dot silicate thin film according to claim 1, wherein the coating of the quantum dots onto the substrate is carried out by drop casting, spin coating, dip coating, spray coating, flow coating or screen printing.

7. The method for producing a quantum dot silicate thin film according to claim 1, wherein the sol-gel process involves hydrolysis and condensation in the presence of a catalyst, the molar ratio of the catalyst to the monomer is within the range of 1:0.000001~1:10, the equivalent amount of water is in the range of 1.0~100.0 relative to the reactive groups present in the monomer, the reaction temperature is in the range of 0~200° C., and the reaction time is in the range of 1~100 hours.

8. A method for producing a quantum dot silicate thin film which comprises the steps of:
    subjecting a silane compound and a siloxane-based monomer to a sol-gel process to form a silicate precursor, the silane compound having a phosphine-, amine- or thiol-based functional group and at least one reactive group for a sol-gel process;
    mixing the silicate precursor and semiconductor quantum dots having a size of 1~100 nm synthesized by a wet chemistry technique;
    coating the mixture onto a substrate; and
    heat-treating the coated substrate.

9. The method for producing a quantum dot silicate thin film according to claim 8, wherein the quantum dots are made of a material selected from the group consisting of cadmium selenide (CdSe), cadmium sulfide (CdS), cadmium telluride, (CdTe), zinc selenide (ZnSe), zinc sulfide (ZnS), zinc telluride (ZnTe), mercury telluride (HgTe) and mixtures thereof.

10. The method for producing a quantum dot silicate thin film according to claim 8, wherein the silane compound having a phosphine-, amine- or thiol-based functional group and at least one reactive group for the sol-gel process is represented by the following formula 1:

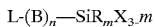  [Formula 1]

wherein L is a thiol group, a dialkylphosphinyl group having 1~5 carbon atoms, or a dialkylamine group having 1~5 carbon atoms; B is methylene or siloxy (—Si—O—) group; n is an integer of 1 to 50; X is a halogen atom or an alkoxy group having 1~10 carbon atoms; R is an alkyl group having 1~10 carbon atoms; and m is an integer of 0 to 2.

11. The method for producing a quantum dot silicate thin film according to claim 10, wherein the silane compound is at least one compound selected from the group consisting of mercaptomethylmethyldimethoxysilane, 3-mercaptopropylmethyldimethoxysilane, 3-mercaptopropyltriethoxysilane, 3mercaptopropyltrimethoxysilane, 2-diphenylphosphinoethyltriethoxysilane, diphenylphosphinoethyldimethylethoxysilane, 3-aminopropylmethyldiethoxysilane, 3-aminopropyldimethylethoxysilane, 3-aminopropyltriethoxysilane, 3-aminopropyltrimethoxysilane, 3-aminobutyltrimethoxysilane, 3-(m-aminophenoxy) propyltrimethoxysilane and n(2-aminoethyl)-3-aminopropylmethyldimethoxysilane.

12. The method for producing a quantum dot silicate thin film according to claim 8, wherein the substrate on which the quantum dot thin film is produced is glass, quartz, a silicon (Si) wafer, a silica-coated substrate or an alumina-coated substrate.

13. The method for producing a quantum dot silicate thin film according to claim 8, wherein the coating of the quantum dots onto the substrate is carried out by drop casting, spin coating, dip coating, spray coating, flow coating or screen printing.

14. The method for producing a quantum dot silicate thin film according to claim 8, wherein the sol-gel process involves hydrolysis and condensation in the presence of a catalyst, the molar ratio of the catalyst to the monomer is within the range of 1:0.000001~1:10, the equivalent amount of water is in the range of 1.0~100.0 relative to the reactive groups present in the monomer, the reaction temperature is in the range of 0~200° C., and the reaction time is in the range of 1~100 hours.

15. The method for producing a quantum dot silicate thin film according to claim 8, wherein the siloxane-based monomer is a ring-structured siloxane monomer represented by the following formula 2:

[Formula 2]

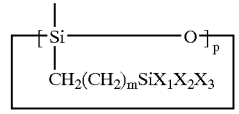

wherein R is a hydrogen atom, an alkyl group having 1~3 carbon atoms, a cycloalkyl group having 3~10 carbon atoms or an aryl group having 6~15 carbon atoms; $X_1$, $X_2$ and $X_3$ are each independently an alkyl group having 1~3 carbon atoms, an alkoxy group having 1~10 carbon atoms or a halogen atom, provided that at least one of $X_1$, $X_2$ and $X_3$ is hydrolysable; p is an integer of 3 to 8; and m is an integer of 0 to 10, or a cage-structured siloxane monomer represented by the following formulae 3 to 5:

[Formula 3]
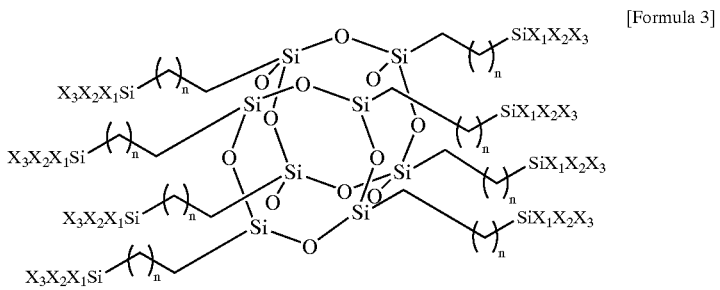

[Formula 4]
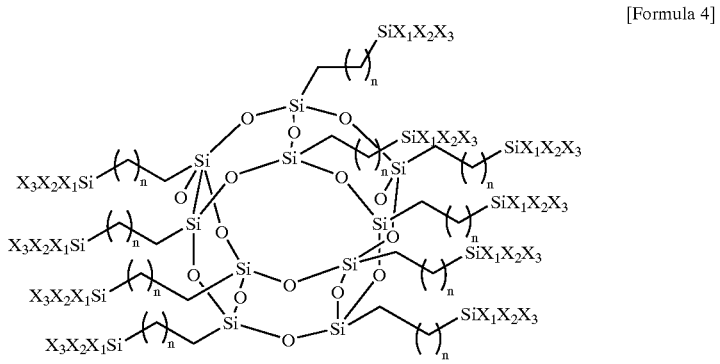

[Formula 5]
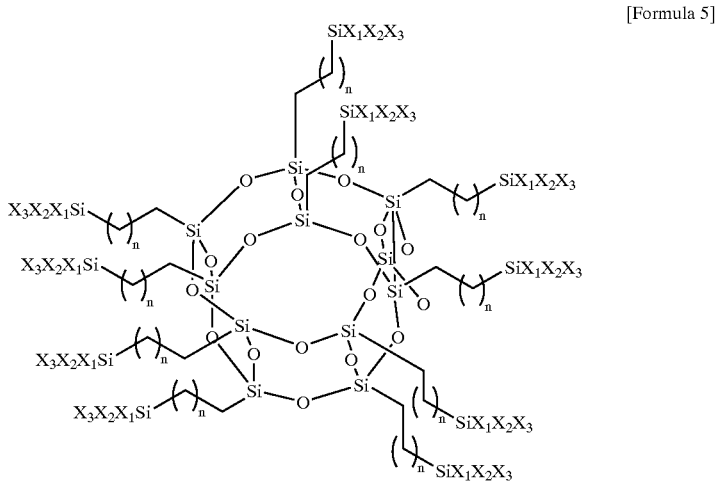

wherein $X_1$, $X_2$ and $X_3$ are each independently an alkyl group having 1~3 carbon atoms, an alkoxy group having 1~10 carbon atoms or an halogen atom, provided that at least one of $X_1$, $X_2$ and $X_3$ is hydrolysable; and n is an integer of 0 to 10, and if necessary, a silane compound is added to the siloxane-based monomer, represented by the following formulae 6 to 8:

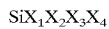      [Formula 6]

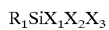      [Formula 7]

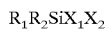      [Formula 8]

wherein $R_1$ and $R_2$ are each independently a hydrogen atom, an alkyl group having 1~3 carbon atoms, a cycloalkyl group having 3~10 carbon atoms or an aryl group having 6~15 carbon atoms; and $X_1$, $X_2$, $X_3$ and $X_4$ are each independently an alkoxy group having 1~10 carbon atoms or a halogen atom.

16. The method for producing a quantum dot silicate thin film according to claim 8, wherein the silane compound and the siloxane-based monomer is reacted in the molar ratio of 99:1–1:99.

17. The method for producing a quantum dot silicate thin film according to claim 8, wherein the silicate precursor and the quantum dots are mixed in the weight ratio of 99:1–50:50.

18. A quantum dot silicate thin film produced by the method of claim 1.

19. A quantum dot silicate thin film produced by the method of claim 8.

* * * * *